US006712071B1

(12) United States Patent
Parker

(10) Patent No.: US 6,712,071 B1
(45) Date of Patent: Mar. 30, 2004

(54) SELF-CONTAINED BREATHING APPARATUS

(75) Inventor: Martin John Parker, Leeside, Lowertown, Helston, Cornwall TR13 OBY (GB)

(73) Assignees: Martin John Parker, Cornwall (GB); David Parker, Cornwall (GB); Angela Margaret Parker, Cornwall (GB)

( * ) Notice: Subject to any disclaimer, the term of this patent is extended or adjusted under 35 U.S.C. 154(b) by 0 days.

(21) Appl. No.: 09/508,983

(22) PCT Filed: Sep. 17, 1998

(86) PCT No.: PCT/GB98/02822

§ 371 (c)(1),
(2), (4) Date: May 15, 2000

(87) PCT Pub. No.: WO99/13944

PCT Pub. Date: Mar. 25, 1999

(30) Foreign Application Priority Data

Sep. 18, 1997 (GB) ............................................ 9719824

(51) Int. Cl.[7] .......................... A61M 16/00; A62B 7/00; F16K 31/02

(52) U.S. Cl. ........................... 128/204.21; 128/201.25; 128/201.27; 128/201.28; 128/203.14; 128/204.26; 128/205.11; 340/508

(58) Field of Search ....................... 128/201.25–201.28, 128/203.14, 204.21, 204.22, 204.26, 205.11, 205.12, 205.22–205.24, 205.27, 205.28; 340/506–508, 573.1, 539

(56) References Cited

U.S. PATENT DOCUMENTS

| | | | | | |
|---|---|---|---|---|---|
| 3,556,098 | A | | 1/1971 | Kanwisher | |
| 3,674,022 | A | * | 7/1972 | Dounoucos | 128/204.22 |
| 3,695,261 | A | * | 10/1972 | Emmons | 128/205.23 |
| 3,923,053 | A | * | 12/1975 | Jansson | 128/201.27 |
| 3,957,043 | A | * | 5/1976 | Shelby | 128/205.23 |
| 4,056,098 | A | * | 11/1977 | Michel et al. | 128/205.23 |
| 4,108,171 | A | | 8/1978 | Nyman | |
| 4,236,546 | A | * | 12/1980 | Manley et al. | 137/88 |
| 4,327,437 | A | * | 4/1982 | Frosch et al. | 714/3 |
| 4,336,590 | A | * | 6/1982 | Jacq et al. | 128/204.21 |
| 4,402,903 | A | * | 9/1983 | Lenderking | 376/245 |
| 4,423,723 | A | * | 1/1984 | Winkler et al. | 128/202.22 |
| 4,440,166 | A | * | 4/1984 | Winkler et al. | 128/204.22 |
| 4,454,878 | A | * | 6/1984 | Morrison | 128/201.27 |
| 4,621,643 | A | * | 11/1986 | New, Jr. et al. | 600/32 |
| 4,700,708 | A | * | 10/1987 | New, Jr. et al. | 600/32 |
| 4,770,179 | A | * | 9/1988 | New, Jr. et al. | 600/32 |
| 4,794,376 | A | * | 12/1988 | Lloyd et al. | 340/508 |
| 4,797,670 | A | * | 1/1989 | Joyner | 340/3.71 |
| 4,939,647 | A | * | 7/1990 | Clough et al. | 364/413.31 |
| 4,964,404 | A | * | 10/1990 | Stone | 128/204.22 |
| 4,974,585 | A | * | 12/1990 | Stone | 128/205.12 |
| 5,036,841 | A | * | 8/1991 | Hamilton | 128/202.26 |
| 5,127,398 | A | * | 7/1992 | Stone | 128/204.18 |

(List continued on next page.)

FOREIGN PATENT DOCUMENTS

| | | |
|---|---|---|
| EP | 0 318 157 | 5/1989 |
| GB | 2 201 602 | 9/1988 |

*Primary Examiner*—Aaron J. Lewis
*Assistant Examiner*—Joseph Weiss
(74) *Attorney, Agent, or Firm*—Gifford, Krass, Groh, Sprinkle, Anderson & Citkowski, P.C.

(57) ABSTRACT

A Self Contained Re-breathing apparatus with a single bank of oxygen sensors for signaling oxygen contact back to a display and oxygen valve control, where the signal is set via two identical and independent sets of signal control circuitry which are interconnected in a primary and secondary relationship. The primary circuitry controlling the valve and the secondary circuitry sending a signal to a display, wherein the two identical and independent sets of circuitry can perform each role and serve to confirm the satisfactory operation of a master signal processing circuit.

20 Claims, 6 Drawing Sheets

U.S. PATENT DOCUMENTS 5,315,988 A * 5/1994 Clarke et al. .......... 128/204.23
5,368,018 A * 11/1994 Stone .................... 128/201.28
5,485,834 A * 1/1996 Joye et al. ............. 128/205.13
5,503,145 A * 4/1996 Clough .................. 128/204.22
5,570,688 A * 11/1996 Cochran et al. ....... 128/205.23
5,887,611 A * 3/1999 Lampotang et al. .......... 137/93
5,924,418 A * 7/1999 Lewis ................... 128/204.22
6,003,513 A * 12/1999 Readey et al. ......... 128/205.24
6,176,234 B1 * 1/2001 Salter et al. ........... 128/200.18
6,199,550 B1 * 3/2001 Wiesmann et al. .... 128/204.23
6,283,120 B1 * 9/2001 Kellon .................. 128/204.28
6,302,106 B1 * 10/2001 Lewis ................... 128/204.22
6,360,182 B1 * 3/2002 Hales ......................... 702/139
6,396,398 B1 * 5/2002 Donat et al. ................ 340/508

* cited by examiner

SELF-CONTAINED BREATHING APPARATUS

The present invention relates to self-contained breathing apparatus such as may be used for underwater diving or in other hostile environments in which a user may need a supply of breathable gas. Such uses include fire fighting where the atmosphere may be heavily polluted with combustion products and noxious gases, other industrial environments where the atmosphere may be polluted or otherwise unbreathable, or at high altitude where the atmosphere itself is too thin or effectively non-existent.

Although applicable to a wide range of other uses the present invention will be described hereinafter with particular reference to its application to underwater breathing apparatus for diving applications. It will be understood, however, that this description is provided without prejudice to the generality of the invention or its range of applications.

It is well known to provide divers with self-contained underwater breathing apparatus in order to prolong the time for which they can remain below the surface of the water. The most widely used self-contained breathing apparatus comprises a rigid container within which is housed a supply of compressed air which is allowed out of the container via a high pressure or first stage regulator and directed through a flexible hose to a mouthpiece containing a demand valve including a second stage regulator which acts automatically to open and close as the diver inhales and exhales. Such systems are known as open-circuit breathing apparatus because exhaled gas is allowed to pass directly out into the marine environment so that a stream of bubbles is emitted upon each exhalation. If the compressed gas breathed from the gas container is air a large proportion of the exhaled gas will constitute nitrogen which is present in air in an approximate ratio of 4:1 with oxygen as is well known. In other words 80% of the air which is breathed by the diver, and therefore 80% of the content of the compressed air container, or air bottle, comprises little more than a vehicle for the oxygen some of which is converted to carbon dioxide during its residence in the lung. Thus 80% of the breathed gas is not really needed by the body except to dilute the oxygen. It is not possible to breath pure oxygen below 10 m since at higher pressures oxygen is toxic.

Proposals have in the past been made for so-called closed circuit or "re-breather" apparatus in which the carbon dioxide content of exhaled air is removed from the exhaled air outside the body, fresh oxygen is introduced to replace that consumed, and the thus-reconditioned air returns to the diver for re-breathing. In this way it is necessary for the diver only to carry two or three lungfuls of nitrogen sufficient to circulate around the closed circuit. Such a system is described, for example, in U.S. Pat. No. 4,964,404 to William C Stone and in U.S. Pat. No. 3,555,098 to John W Kanwisher and Walter A Starck II. These Patentees were not the first to devise closed circuit re-breather apparatus, however, it being known that so-called "frogmen" used re-breather apparatus during World War 2 in order to avoid the tell-tale bubbles rising to the surface upon exhalation in an open-circuit system such as the traditional compressed air bottle arrangement described above. U.S. Pat. No. 4,964,404 describes an improved such mixed gas breathing apparatus in which a container for exhaled gas (the so-called counterlung) is formed in two parts, a first part communicating with a hose leading from a mouthpiece to a carbon dioxide removal filter, and a second part in the line between the carbon dioxide removal filter and the mouthpiece. The carbon dioxide removal filter in the system described in U.S.

Pat. No. 3,556,098 includes a chamber housing oxygen partial pressure sensors used to detect the oxygen content in the exhaled gas and to reinstate the oxygen balance by introducing oxygen through a valve controlled indirectly by the sensors. The oxygen sensor system is described as comprising three sensors with the average value of the sensor signals being taken to produce the control signal. Three sensors are used on the grounds that the appropriate introduction of the right amount of oxygen is so critical, in these circumstances, that it is not possible safely to rely on the signal from a single sensor or even two sensors because any failure of a sensor may not be detected or recognised sufficiently quickly to prevent inadequate oxygenation of the circulating gas, or excess oxygenation depending on the nature of the failure. The argument presented for utilising three sensors is that by taking the average of three sensors the departure from the correct value introduced by a single faulty sensor is minimised. The effect of a faulty sensor on the average value is limited by electronically "clipping" the values to predetermined maximum and minimum values. The three sensors are monitored so that should one start to produce a signal which differs materially from that produced by the other two an alarm is indicated and the dive can be aborted. This strategy is based on the fact that the probability of two sensors being faulty is low, and the probability of two sensors being faulty at the same time is lower and can be reduced even further by taking remedial action immediately a faulty sensor is detected.

However, although this makes concessions to absolute safety by using an alarm signal upon departure of one sensor beyond a predetermined threshold from the other two, this results in the need for the diver to make a judgement on whether the other two sensors are performing properly and risks disruption to the diving activity unless the remaining two sensors are so clearly providing the correct control signal that the diver can come to the conclusion that he can safely ignore the third. The safety strategy adopted by W Stone in U.S. Pat. No. 4,964,404 is further reinforced by the provision of two entirely separate closed circuit re-breather systems each having front and back counterlungs and each being adapted to utilise components of the other system in the event of failure. Such 100% redundancy is necessitated by the chosen strategy in the management of the sensor signals and results in considerable additional equipment expense and bulk.

The present invention seeks to provide self-contained breathing apparatus of the closed-circuit re-breather type in which an improved strategy for management of the oxygen sensors is adopted which, whilst recognising the possibility of failure of an oxygen sensor, monitors the operation in a more practical manner and avoids the necessity for the duplication of all the components without loss of safety. Indeed, safety of the diver remains of paramount importance and numerous features of the apparatus formed in accordance with the present invention are directed at minimising the risk to the diver whilst nevertheless avoiding the need unnecessarily to resort to open circuit emergency breathing due to minor malfunctioning of equipment.

According to a first aspect of the present invention, there is provided self-contained breathing apparatus of the type having a container for receiving exhaled gas, means for removing carbon dioxide from the exhaled gas, sensor means for detecting the oxygen content of the exhaled gas and means for injecting oxygen into the exhaled gas to reinstate the oxygen content so as to lie within a desired range for re-breathing, in which the signals from the oxygen sensor means are delivered to two independent signal processing circuits which are interconnected in a primary and secondary relationship with the primary signal processing circuit acting in use to control the operation of a solenoid valve for injection of oxygen into the exhaled gas and the secondary signal processing circuit acting in use to display information concerning the sensor output signals to provide confirmation of the satisfactory operation of the master signal processing circuit.

Preferably the said signal processing circuits are interconnected with a signal line and the secondary signal processing circuit is able constantly to monitor the operation of the primary signal processing circuit.

Through this interconnecting signal line the two signal processing circuits are able to communicate with one another, the processors incorporated therein being programmed to check, upon being switched on, whether any signals are being received from the other circuit. If not it acts as the primary controller and commences transmitting signals to the other signal processing circuit to identify this condition. Each signal processing circuit has an independent on/off switch and is programmed to adopt the role of primary circuit if the other signal processing circuit is not switched on or is malfunctioning for example due to power failure at the primary circuit or if the diver should (perhaps inadvertently) switch off the original master.

The present invention also comprehends self-contained breathing apparatus of the type in which exhaled gas is reconditioned by the introduction of oxygen to prepare it for re-inhalation and the oxygen content is constantly monitored by oxygen sensors the output from which is used to control the reintroduction of oxygen into the gas to prepare it for re-breathing, in which the oxygen sensor means comprise three independent sensors housed in a chamber through which the gas to be reconditioned flows in use of the apparatus, and the outputs of the sensors are delivered to signal processing circuits which act to determine the value of the partial pressure of oxygen in the gas in the chamber by taking the average value of whichever of the two sensor outputs are nearest to one another in value.

The argument for using three sensors is developed in U.S. Pat. No. 3,556,098 although a rather different operational strategy is utilised in the present invention. If only one sensor were present there would be no way of determining whether its output is right or wrong, and even if two sensors are used there is still no way in which a utiliser can determine, if the two sensors provide different outputs, which one is correct and which one is not. In U.S. Pat. No. 3,556,098 three sensors are utilised and the average of all three taker, with the output signals being limited or "clipped" so that should they depart from a predetermined set value by more than this predetermined deviation the effect which a sensor producing an erroneous signal will have on the average is minimised. This nevertheless allows the erroneous sensor to have some influence on the average and, furthermore, introduces a potentially dangerous situation if all sensors correctly indicate a value outside the preset range since the system will act to limit their signals to the preset limits. In the system according to the present invention the signal from the sensor which differs from each of the other two by the greatest amount is ignored; this allows a diver still to make use of the rebreather equipment when a faulty sensor is detected (this could be an alarm signal) whilst still having reasonable confidence that the equipment as a whole is functioning correctly so that should it be necessary to undertake decompression stops or if there is an extended route (for example out of an underwater cave system) before the diver can surface it is not necessary to resort to the open circuit breathing equipment which may not have sufficient capacity for an extended exit procedure.

Preferably the oxygen control system acts to maintain a nominal oxygen partial pressure at a lower range in the region of 0.7 bar. In practice the equipment may be set to a lower value range of 0.5 to 0.9 bar. Likewise the upper limit is preferably 1.3 bar and in practice the equipment may be set to an upper value range of 0.9 to 1.5 bar. The system has two set points, high and low, in order to allow the use of the equipment at the surface and for descent as well as at depth. The low setting is used at the surface and during the descent whilst the high set point is utilised at depth and may be selected by means of a manual switch or may be automatically initiated by a pressure sensor. When the equipment is first turned on the low set point is automatically set at 0.7 bar and the high value at 1.3 bar. The purpose of providing a low set point for use at the surface and during descent is to avoid wasting oxygen, and also to allow the diver to conduct the descent at a reasonably fast rate without the oxygen pressure rising too high. The higher set point then gives oxygen-rich diving down to the normal maximum depths for sport diving (namely 45–50 meters) and also provides a reasonably oxygen-rich decompression, typically at about 81% $O_2$ at 6 meters. The equipment is preferably provided with means for adjusting the high and low set points to allow divers to make adjustments to suit their particular purposes. Adjustments can be made under water if required.

In a preferred embodiment of the invention the sampling frequency at which the signals are processed is maintained at a level such that the valve controlled by the output signal from the sensors may be activated immediately in response to a change in the oxygen partial pressure.

The oxygen sensing arrangement preferably includes three oxygen sensors which are positioned spaced around a central location in a chamber, facing inwards so that when in the normal position of use, with the diver facing downwards, all three sensors face downwards, each being provided with an individual moisture deflector on the sensor face and waterproofing means on the connections and control circuits. It is also preferred that the sensors are positioned in such a way that the whole of the sensor is located in the chamber. In this way inaccuracies due to temperature gradients across the sensor face or body are eliminated. A vibration-proof locking device for the electrical connections, which will be described in more detail below is also provided.

The rebreather apparatus of the present invention preferably includes a source of a breathable diluent gas.

There may be provided means by which the diluent gas can be directed over the oxygen sensors upon introduction into the chamber, whereby to encourage drying of any moisture on the sensors.

The diluent gas may be air, Heliox or Trimix but is intended to be breathable at the target depth to afford a first open circuit emergency breathing gas source.

In another aspect the present invention provides self-contained breathing apparatus of the type comprising a mouthpiece, a counterlung, carbon dioxide extraction means, oxygen sensing and reintroduction means acting to maintain the oxygen partial pressure at or in the vicinity of a predetermined value to allow re-breathing of the gas from the counterlung, in which the counterlung is separated into two independent chambers one receiving exhaled gas from the mouthpiece and the other receiving gas from the carbon dioxide removing means, after introduction of oxygen, to act as a temporary store of gas reconditioned for breathing, in which the two counterlung chambers are connected to the mouthpiece by hose couplings incorporating two unidirectional valves orientated to ensure that air exhaled into the mouthpiece is directed only to the exhaled air counterlung and air inhaled through the mouthpiece arrives only from the reconditioned air counterlung, and in which the interconnection between an air hose and the counterlung is made by way of a T-coupling which is swivelable to allow free movement of the air hoses, which particularly facilitate assembly.

In any of the above aspects or embodiments there may be a T-coupling between each air hose and the associated counterlung which includes an internal baffle directing air within the hose to or from the counterlung and further acting as a moisture trap.

In the preferred embodiment of the invention the means for removing carbon dioxide from the exhaled gas encomprises a filter bed housed between circular permeable barriers in a cylindrical container having a central axial member.

The flexible container for receiving exhaled gas may be a shaped counterlung adapted to pass over the shoulder of a diver utilising the apparatus. The apparatus of the invention will in fact function satisfactorily whether the preliminarily shaped counterlung is mounted at the front or at the back of the diver, or passes over the shoulder. The pre-shaped "over-the-shoulder" configuration is preferred because this ensures that the counterlungs are as close as possible to the lung centroid in the majority of swimming positions thereby reducing static lung loading. The signal processing circuits preferably include monitors for detecting if the oxygen partial pressure departs from a predetermined range whereby to provide an alarm signal, and an audible alarm indicator is positioned close to the diver's ear. This may be within the oxygen sensor casing or within the air hoses leading to and/or from the mouthpiece. These hoses may be afforded protection by a fabric sleeve which may be pre-shaped to a curved configuration. Such pre-shaped sleeves may be removable by the provision of elongate fasteners along their length.

To make it suitable for use by a diver the means for removing carbon dioxide, the oxygen sensors and control valve, a container housing a source of oxygen under pressure, and a container housing a breathable diluent gas are all supported on a panel having means by which the apparatus can be carried on the back of a wearer. This may be a buoyancy jacket, or a harness or straps. If straps or a padded harness are used then an additional buoyancy compensator preferably fits between the harness and the back frame of the apparatus of the invention. The counterlungs may be separate from the body harness, in which case the body harness passes through loops on the underside of the counterlungs. In other embodiments the counterlungs may be formed as the shoulder portion of the body harness. In such embodiments a heavier duty buckle is required at the bottom of the counterlungs. The panel may be part of a substantially rigid casing which protects the components from impacts or knocks in use and provides a more "streamline" external appearance.

One embodiment of the present invention will now be more particularly described, by way of example, with reference to the accompanying drawings, in which.

Figure 3:
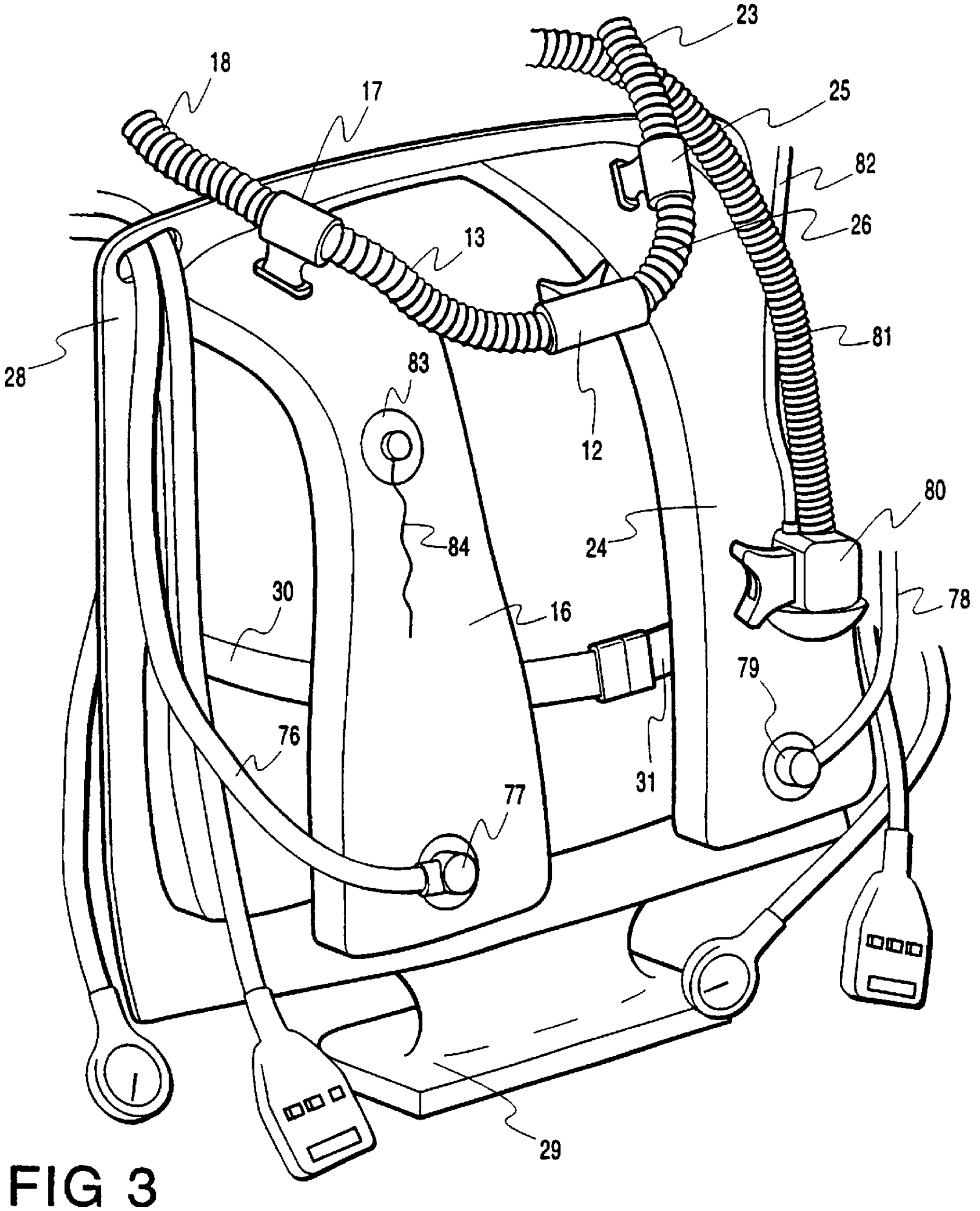
FIG. 3 is a three quarter perspective view of the embodiment showing the apparatus from the front and one side.
Figure 3A:
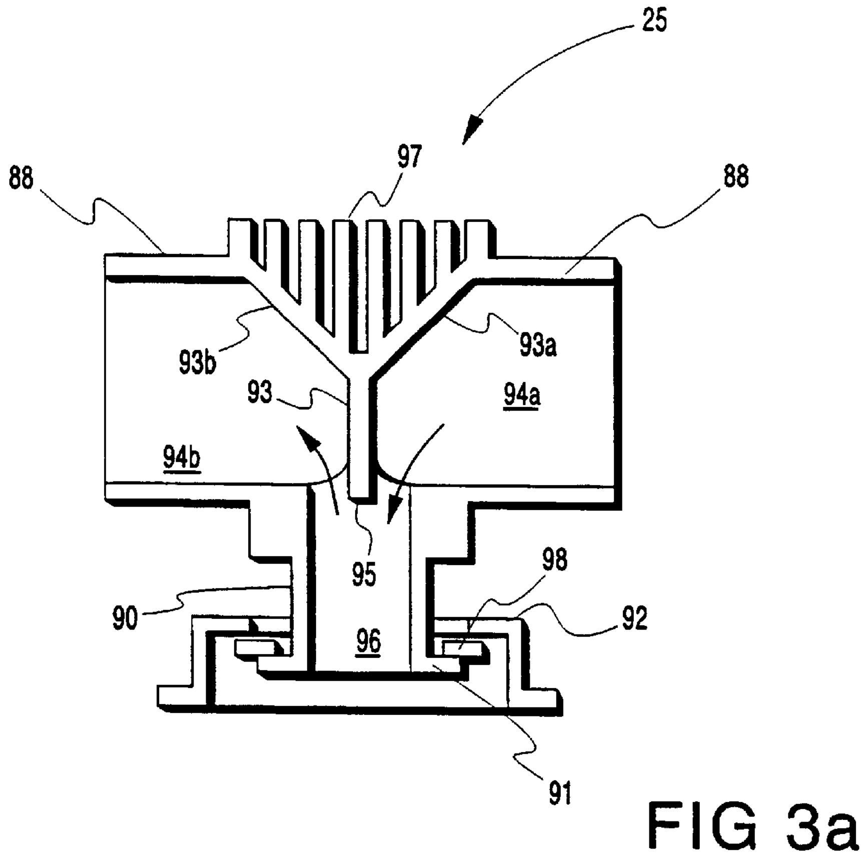
Figure 4:
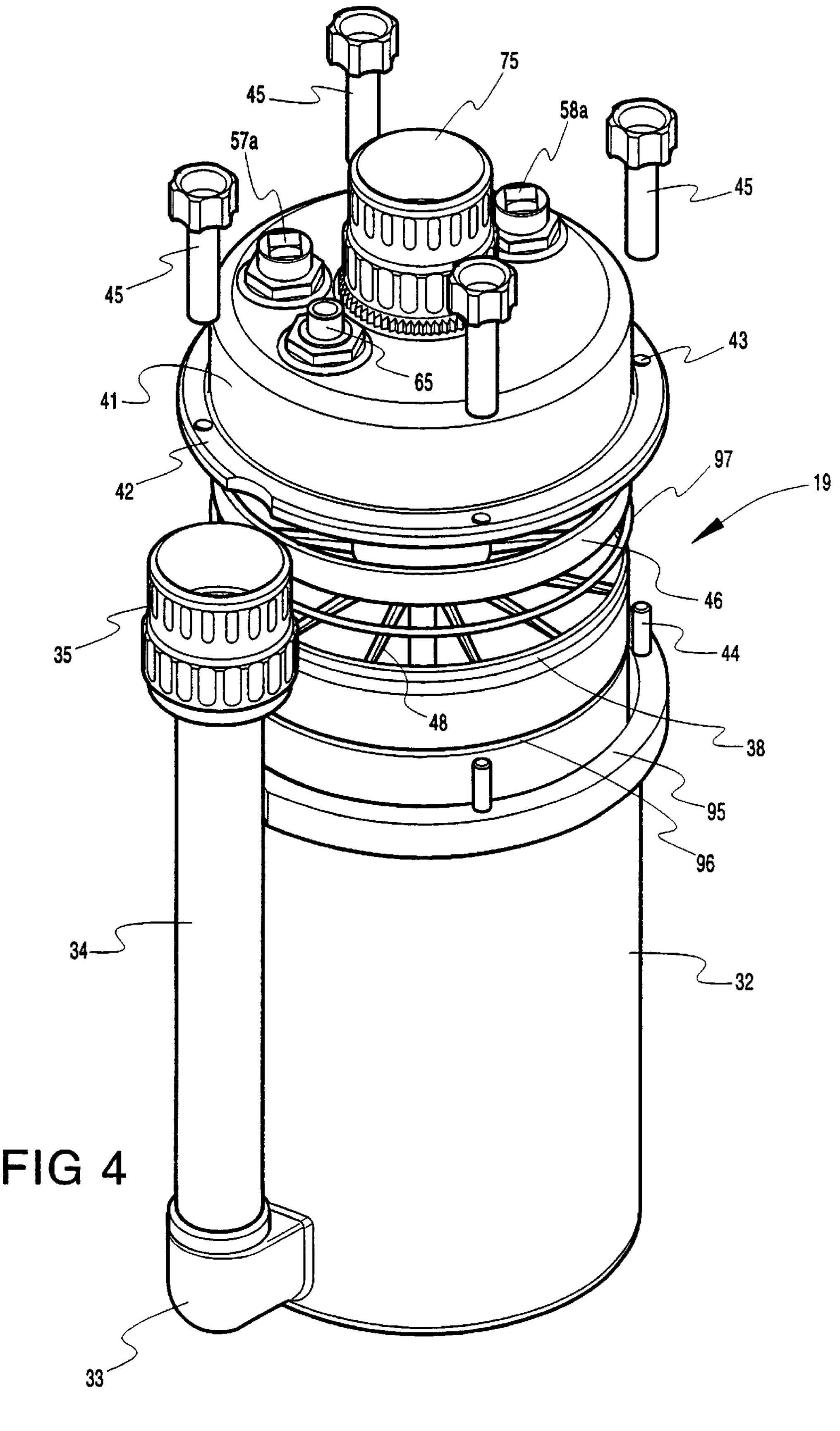
Figure 5:
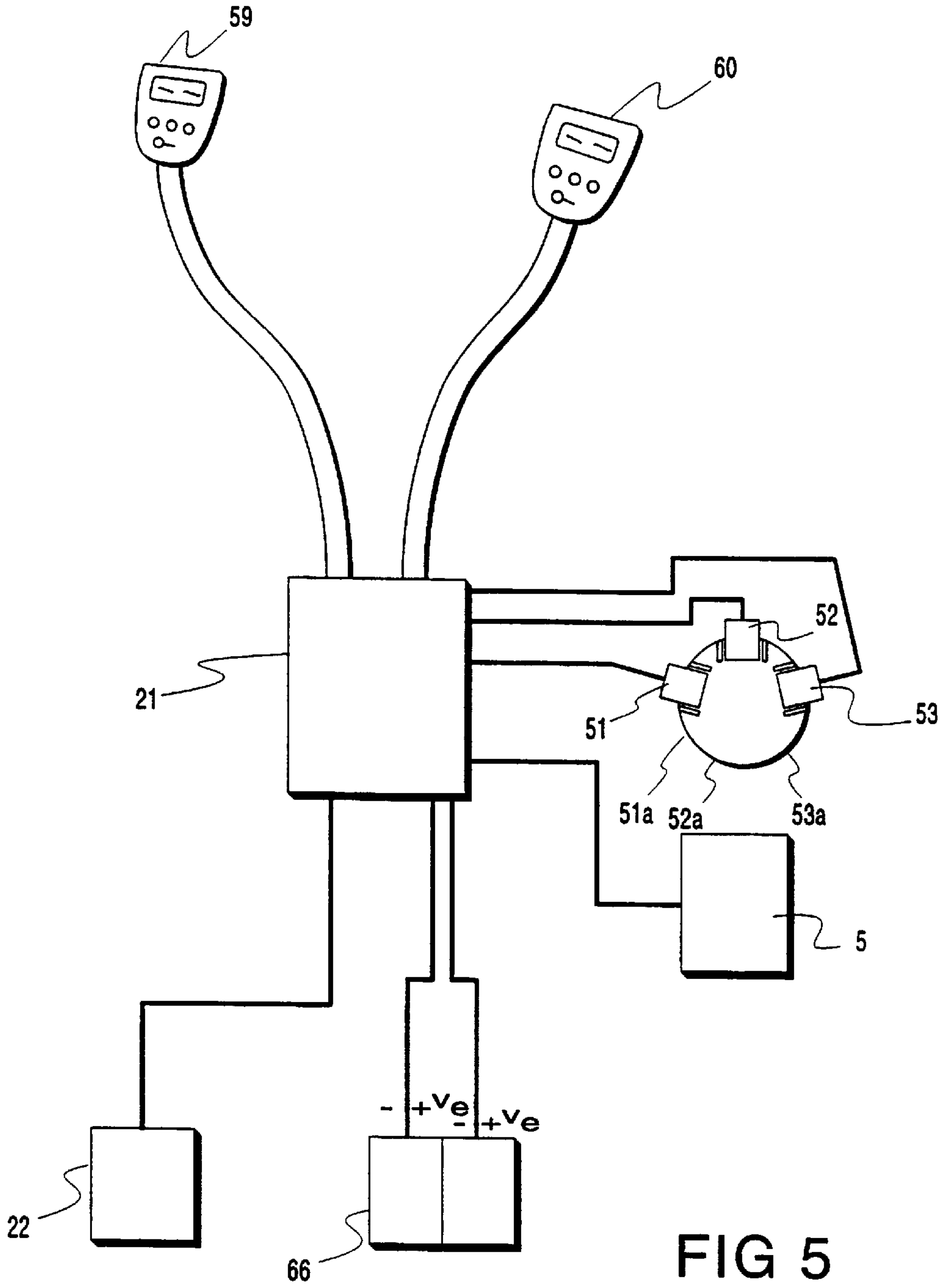

FIG. 3*a* is a sectional view of a swivelable hose coupling forming part of the embodiment of the invention;

FIG. 4 is a perspective view of the carbon dioxide treatment apparatus forming part of the embodiment of the invention; and FIG. 5 is a schematic circuit diagram showing the major elements of the control circuit of the re-breather apparatus of the present invention.

Figure 1:
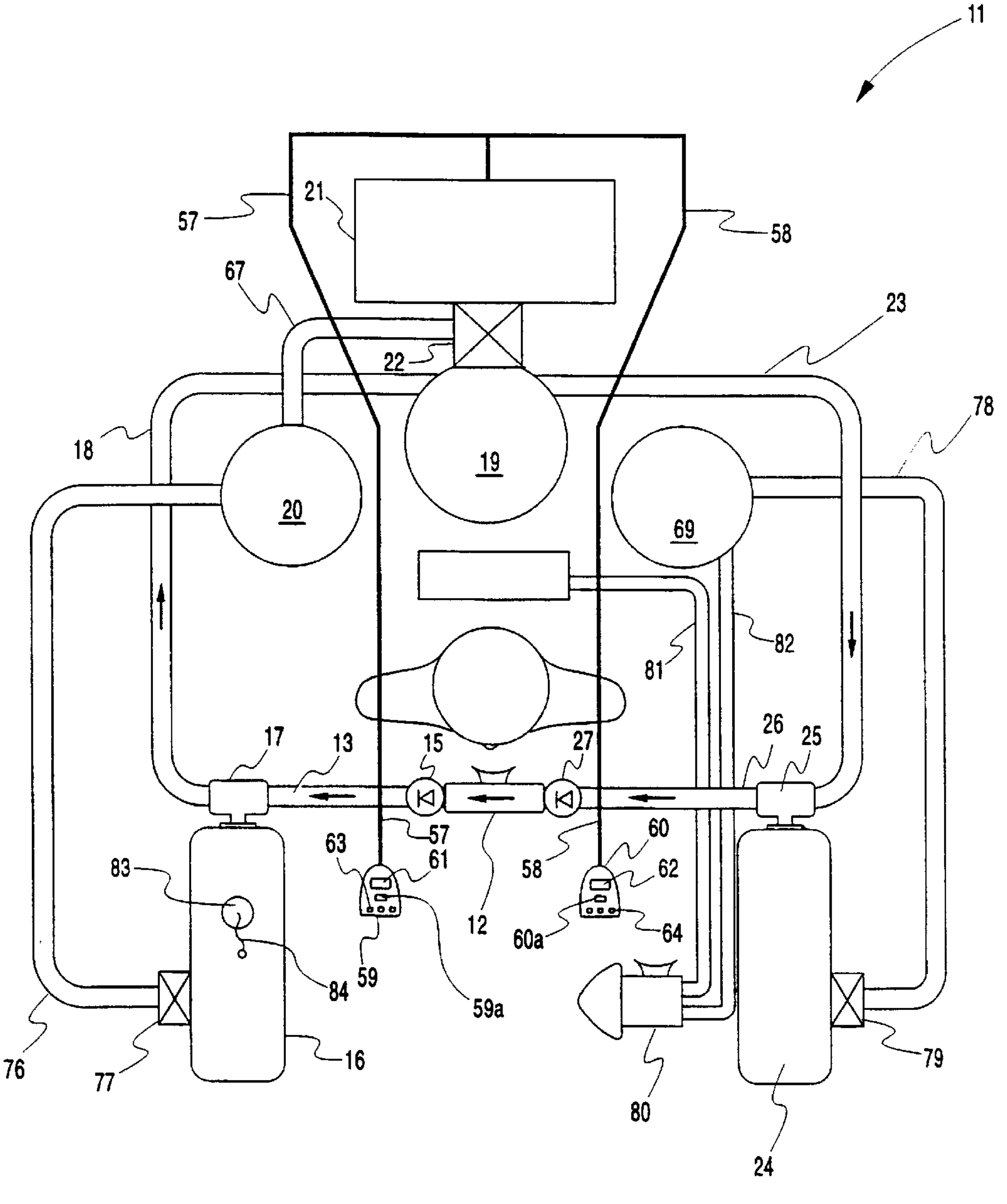
FIG. 1 is a schematic diagram illustrating a circuit for a self-contained re-breather formed as a first embodiment of the present invention.

Referring first to FIG. 1, self-contained re-breather apparatus generally indicated with the reference numeral 11 comprises a closed circuit leading from a mouthpiece 12 along an air hose 13 within which is a unidirectional valve indicated schematically 15 and connected to an exhaled-gas counterlung 16 by a T-coupling 17 the form of which can be seen more clearly in FIG. 3*a*.

From the T-coupling 17 of the exhaled gas counterlung 16, which in use contains oxygen-depleted exhaled gas, extends a connector hose 18 leading to a gas reconditioning unit 19 which will be described in more detail in relation to FIGS. 2 et seq. In the gas reconditioning unit 19 carbon dioxide in the exhaled gas is removed and oxygen from a reservoir 20 is introduced (under the control of a control system which will be described in more detail below) via a solenoid valve 22 in a manner which will be described in more detail below. The reconditioned gas is drawn from the unit 19 via an air hose 23 and delivered to a second counterlung 24 in the form of a flexible sac joined to the hose 23 by another T-coupling 25 which, like the T-coupling 17 is swivelable to allow free movement of the air hose during use and for ease of assembly. The form of this T-coupling is shown in more detail in FIG. 3*a*. From the T-coupling 25 a breathing hose 26 leads to the mouthpiece 12 via a further unidirectional valve 27 shown schematically in FIG. 1.

As will be seen from FIGS. 2 to 5, the counterlungs 16, 24 are formed as shaped flexible bladders which pass over the shoulders and the front panels of a jacket-like garment the rear of which is secured to a rigid panel 28 having a rearwardly projecting shelf 29 and straps 30, 31 for passing around the torso of a wearer to secure the apparatus in place.

FIG. 3*a* illustrates in cross-section the form of the swivel T-coupling 25 in more detail. This comprises a generally T-shape integrally moulded body having two oppositely directed in-line tubular portions 88, 89 with a tubular stem portion 90 extending perpendicularly with respect thereto. The stem portion 90 has a radially outwardly projecting flange 91 and is surrounded by an internally threaded fixing ring 92 by means of which it can be secured to a correspondingly threaded fixing (not shown) on the counterlung. The fixing ring is held in place against removal past the flange 91 by a circlip 98. The two in-line portions 88, 89 define a through flow passage 94 which is separated into two parts 94*a*, 94*b* by a partition 93 integrally moulded with the body and having a free edge 95 dividing the interior passage 96 of the tubular stem portion 90 into two parts. The baffle 93 largely obstructs the through flow passage 94 such that gas arriving from the exhaled air treatment apparatus 19 (that is into the open end of portion 88) is deflected by the baffle 93 into the passage 96 and from there into the counterlung whilst air drawn from the counterlung towards the mouthpiece 12 by inhalation is guided by the baffle 93 into the passage 94*a*. To encourage this movement the baffle 93 has two inclined portions 93*a*, 93*b* and in order to avoid excessively thick material sections upon moulding, the body portion is formed with a plurality of fins 97 defining these inclined baffle walls.

As well as acting as a flow diverter, the baffle 93 also acts, more importantly, as a water trap helping to prevent water which may enter the portion 89, (for example if the mouthpiece is taken out of the user's mouth without being closed) from passing through to portion 88 and on towards the carbon dioxide treatment unit 19. The flow diversion effect of the baffle 93 ensures that water entering the T-coupling is primarily directed towards the counterlung where it can collect harmlessly rather than being allowed readily to pass on to the exhaled air treatment apparatus which contains particulate material detrimentally affected by moisture.

The exhaled air treatment apparatus generally indicated 19 comprises an upright cylindrical container 32 having an inner cartridge 39, which will be described in more detail below, a lower inlet port 33 with a rigid inlet duct 34 extending parallel to the axis of the container 32 and having a releasable coupling 35 for connection to the air hose 18 leading from the T-coupling 17. Within the container 32, as illustrated in the schematic sectional view of FIG. 2, there is a lower chamber 36 into which the port 33 opens and which houses the inner cartridge 39.

At each end of the cartridge 39 is a "spider" 37, 38 which supports respective non-woven gas-permeable, water impermeable filters 49, 50. The cartridge 39 contains a granular material, such as soda lime, which absorbs carbon dioxide. As is well known the reaction can be represented by:

$$2Na(OH)+CO_2 \rightarrow Na_2\,CO_3+H_2O$$

$$2KOH+CO_2 \rightarrow KCO_3+H_2O$$

or $$Ca(OH)_2+CO_2 \rightarrow CaCO_3+H_2O$$

which in excess $CO_2$ gives:

$$CaCO_3+H_2O+CO_2 \rightarrow Ca(HCO_3)_2.$$

Because of the effects of water it is important to keep the granular material within the cartridge dry or at least to limit the amount of wetting. Soaking of the powder material also increases the breathing effort required to breathe through it, and reduces the life of the material. The cartridge 39 has a central stem 100 which ensures even distribution of gas flowing through the cartridge. As can be seen in FIGS. 2 and 4, the container 32 is completed by an upper chamber 40 defined by a chamber cover 41 having a peripheral flange 42 with holes 43 through which project studs 44 extending axially from a similar flange 95 on the container body and by which the cover 41 is secured to the container 32 utilising hollow threaded bolts 45.

Figure 2:
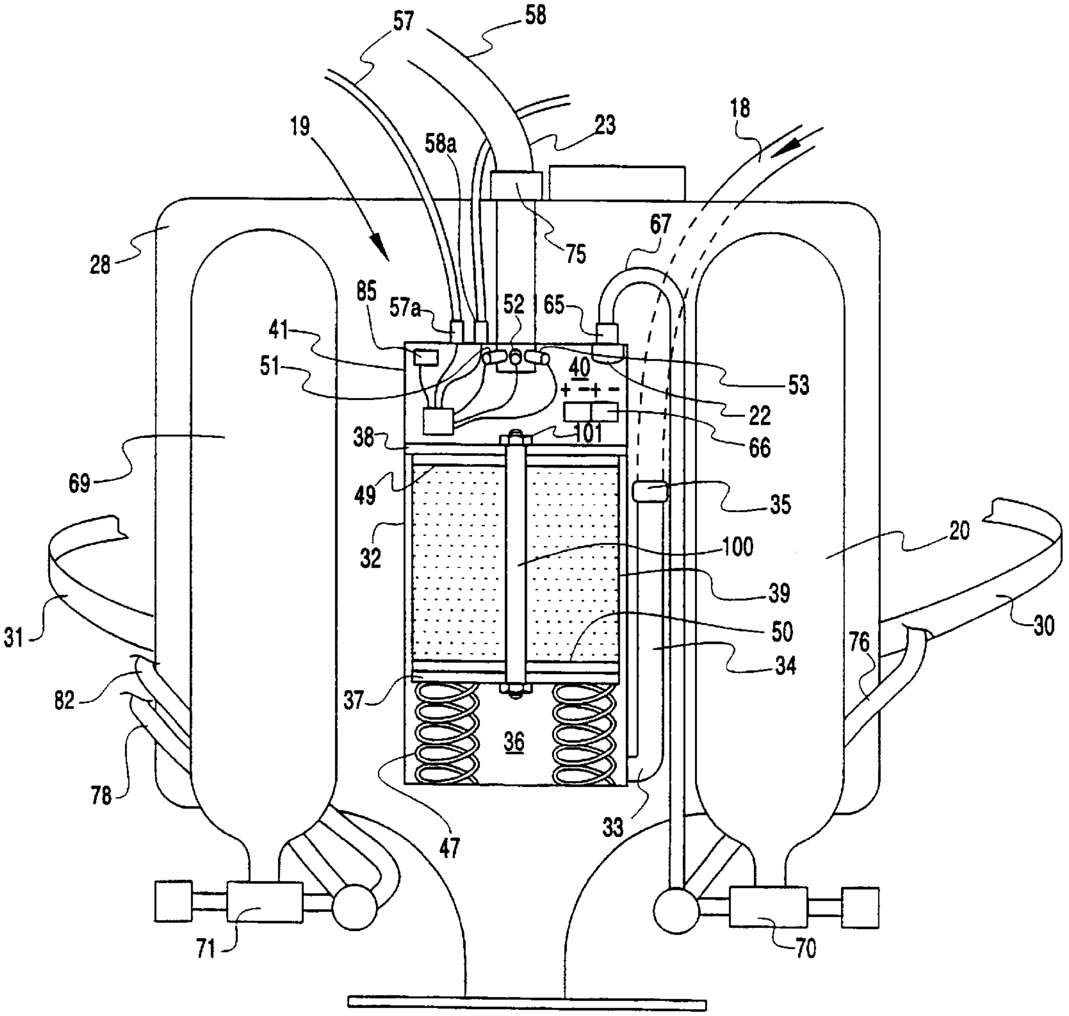
FIG. 2 is a schematic view from the rear of a first embodiment of the invention illustrating the arrangement of the component parts.

Within the container 32 is located a pressure ring 46 engaged by the rim of the cover 41 as the bolts 45 are tightened, which acts to press the top 'spider' 48 of the cartridge 39 downwardly thereby compressing the granular material in the cartridge 39 against the resistance exerted by springs 47 housed in the lower chamber 36 (see FIG. 2). The springs serve to ensure that any settlement to granules is compensated to maintain the granules filling the container with no air pockets. The cartridge 39 is sealed with O-rings at the top, a first 96 around the outside and a second 97 trapped between the upper "spider" 38 and the pressure ring 46. These seals prevent $CO_2$ laden air bypassing the absorbent granular material in the cartridge 39. The gap between the inner cartridge 39 and the wall of the casing 32 provides insulation increasing the absorbent's effective life in cold water. By making the non-woven filter 49, 50, of nylon and the "spiders" 37, 38 of plastics material, this reduces to a minimum any metal components within the interior of the container 32. When used at depth, because of the low temperatures, and because exhaled air has a high moisture content, condensation occurs on all components having a high thermal conductivity, especially metal components, whereas it is important to keep the condensation to a minimum to limit the condensed water affecting the sensors and prevent localised wetting of the granular absorbent material, thereby extending its useful life. Condensation is also combated by the positioning of the oxygen sensors which, as will be understood from a consideration of FIG. 2, all face downwardly (with a slight inclination in the case of sensors 51 and 53) when the diver is in the normal face-down swimming position. The sensor may also be inclined into the diametral plane such that they are inclined to the horizontal when the diver is in an upright position.

Into the chamber 40 projects a central cylindrical tube 87 which acts as a support for three oxygen sensors 51, 52, 53 which are housed in the chamber 40 centrally located in the best position to monitor the oxygen level within the gas returning to the diver via the carbon dioxide removal cartridge 39, namely at the mouth of the exit from the chamber 40. Because the sensors 51, 52, 53 are all mounted within the chamber 40 they experience no temperature gradient, pressure gradient or variations in moisture content and are therefore best located to prevent condensation forming on the sensor face. Each sensor is, in any event, coated with a waterproof "conformal" coating and their respective sensing faces are shrouded with respective guards **51*a*, 52*a*, 53*a*** which assist in deflecting condensation of moisture away from the oxygen sensors.

The signal outputs from the oxygen sensors 51, 52, 53 are lead to a junction panel 21 from where they are applied via signal lines passing through two connections **57*a*, 58*a* to two independent electronic control units 59, 60 having respective displays 61, 62 (see FIG. 1). The signal lines 57, 58 each pass through their own hose to the respective control units or hand sets 59, 60. This eliminates the need for connectors which reduce reliability and increase costs, and also ensures that the pressure within the casing of the handset stays the same as that inside the breathing circuit so that the pressure gradient across the handset casing is minimum at any depth. The control units 59, 60 are carried at the ends of the signal lines 57, 58 which are formed as sheathed waterproof cables having a substantial degree of stiffness allowing the cable to act as an effective support for the control units which are thus merely suspended therefrom. Each control unit 59, 60 has an on/off switch 59*a*, 60*a* and a set of three control buttons 63, 64** respectively for operating the control units as will be described in more detail below.

The cover 41 of the gas processing unit 32 is also provided with a gas port 65, connected by a line 67 to the oxygen cylinder 20. The two gas cylinders 20, 69 have manually operable control valves 70, 71 allowing the oxygen or diluent gas to be turned off when the unit is not in use. The valves are positioned at the lower end of the respective cylinder so that they can be reached easily by a diver in use. The cover 41 also has a main central connector 75 through which treated gas is returned to the main air hose 23 leading back to the oxygen-enriched counterlung 24 and then to the mouthpiece 12 via the breathing hose 26 and the unidirectional valve 27.

The control circuits housed in the control units 59, 60 are identical to one another. The circuit shown in FIG. 5 represents the connection of these units via the junction board 21 to the main components of the system. Each of the control units 59, 60 has a separate battery power supply housed in a common battery casing 66 in the upper chamber 40 within the cover 41 of the gas treatment unit 19. Separate housings could alternatively be provided.

Upon turning on either of the control units 59 or 60 utilising the on/off switch 59*a* or 60*a* the three signals from the oxygen sensors 51, 52, 53 are first monitored and compared. If all three sensors are producing the same signals this consensus is displayed in the screen 61 or 62 together with an indication that the control unit is acting as the master control unit. If the other control unit is then turned on it detects, via the signal lines 57, 58, that the other unit is already in operation, and it sets itself to act simply as a backup or "slave" unit displaying only the independently-determined values of the sensor output signals but not acting to control the solenoid valve 22 by which oxygen is injected from the cylinder 20 into the gas treatment unit 19 to reinstate the oxygen partial pressure to the target value. This function is reserved to the "master" unit which, acting on the basis of the average of the two nearest sensor signals, and ignoring the value of the sensor signal furthest from the consensus determines when oxygen is injected into the chamber 40.

In order to take account of the fact that, over time, with varying pressure and temperature, as well as the varying gas concentrations which they experience, the sensor output signals will be subject to drift so that, even given the same conditions, the sensors will not produce exactly the same output, the system provides a calibration operation which will be described below. Thus, when a control unit is switched on it first checks via the data link provided by the lines 57, 58 whether the other unit is already switched on and in "dive mode"; if this is so the system determines that it is the "slave" and does no further checking as mentioned, simply calibrating itself to the master and thereafter displaying the oxygen partial pressures. However, if the other control unit is not in the "dive mode" the control unit just turned on checks its own battery power supply and the sensor outputs, then waits to receive data from the other control unit. When a control unit is first switched on the data links are checked to establish whether the other control unit is active. If the other control unit is switched off the first unit switched on assumes the role of master and checks its own battery level and the sensor output, and then moves on to the calibration operation mentioned above. This is achieved by flushing the sensor with pure oxygen, detecting the reading of each, and then normalising them. Unlike prior art systems which take up to 30 minutes to calibrate the sensors, which have to be removed from the apparatus in order to be calibrated, the calibration routine in the apparatus of the present invention is completed with the apparatus in the assembled state and takes only approximately 25 seconds. This makes it possible for calibration to be performed immediately before a dive thereby ensuring greatest accuracy. As mentioned above calibration is necessary because the output from the sensors varies over the life of the sensors. Typically, a new sensor may give a reading of say, 13 mV in air, but this may drop to 8 mV towards the end of its life. Moreover, every sensor will produce a slightly different maximum output and therefore must be calibrated to display the "normalised" value when exposed to pure oxygen. The calibration factor for each sensor is then stored and these are compared each time the apparatus is switched on. This comparison also allows the system to take account of the possibility that one of the sensors may suffer a failure or breakdown leading to the generation of an entirely spurious signal. By taking the average of the two nearest signals account can be taken of the fact that the probability of two sensors failing and producing erroneous signals close to one another is very much more remote than the probability of a single sensor failing and producing signals different from the other two. Departure of one sensor from the set range triggers an alarm indicator 85, however, alerting the diver to the situation but allowing him to decide on which course of action to take.

The "master" control unit 59 or 60 can be adjusted using the control buttons 63, 64 to set the desired partial pressure of oxygen as the target for the system to maintain in the chamber 40 thereby controlling the oxygen content of the air passed to the inhalation counterlung 24 and thence to the diver via the mouthpiece 12. At the surface, and down to a depth of about 20 meters, it has been found appropriate to set the target partial pressure of oxygen below 1 bar, normally at 0.7 bar. The unit acts to monitor the average of the two nearest sensors at a high sampling rate and to open the solenoid valve 22 immediately the consensus signal departs by a predetermined small value from the target value so that the desired oxygen content can be closely maintained.

The length of time for which the solenoid valve is energised to introduce oxygen into the system depends on the magnitude of the divergence of the consensus signal from the target value. Moreover, because the valve is opened immediately the predetermined value from the target value is exceeded (which can be very small) the system may operate to introduce oxygen almost immediately the slightest drop in oxygen level is detected. Because of this the oxygen level can be maintained close to the target level without being allowed to stray from the target level or without the system "hunting". This is furthermore enhanced by the provision of a "shut-off power" signal acting to close the solenoid valve, which ensures that the oxygen can be introduced at full rate for the entire time during which the valve is open, with the valve then being snapped shut as soon as the target valve is reached. This allows frequent short injections of oxygen immediately there is a slight variation in the oxygen level so that it can be maintained very close to target at all times.

Once at the target depth, or below 20 m if the target depth is greater than this, it is appropriate to set the target partial pressure to the "high" set point. This is defaulted to 1.3 bar and is done manually but may be done automatically, receiving signals from a suitable external pressure detection unit (not illustrated).

As will be seen in the drawings, the oxygen cylinder 20 is also connected directly by a line 76 to a control valve 77 on the oxygen-depleted counterlung 16. The control valve 77 has a manually-operable push button by which the valve can be opened to allow oxygen to be introduced into the counterlung 16 to override the system. Likewise, the diluent gas container 69 is connected by a line 78 to a manually operable control valve 79 mounted on the inhalation counterlung 24 allowing diluent gas to be introduced into the breathing circuit under the diver's control making up the volume during descent and diluting the oxygen as the diver descends.

The manually operable control valves 77 and 79 are designed to screw on and off the counterlungs. This allows the control valve to swivel in order to obtain the best alignment in use, and also makes it possible for it to be removed to reveal a drain port which can be used for washing and sterilising the counterlungs after use.

The breathing apparatus is also provided with an emergency breathing supply in a known way utilising an automatic valve 80 of known type, for example that described in the Applicant's own European Patent No. 0 318 157 having two hose connections, a first 81 leading to the interior of the buoyancy jacket chamber and a line 82 leading to the diluent gas container 69. The valve 80 is of known type and will therefore not be described hereinafter in detail. It is sufficient here to mention that it contains automatic pressure-sensitive membranes and external control push buttons allowing it to be purged of water entering the mouthpiece whilst the diver is underwater, so that it may be placed in the diver's mouth in place of the mouthpiece 12 should the breathing circuit fail or become of doubtful reliability, whereupon the diver may breathe diluent gas directly from the bottle 69 or, if this should be exhausted, and as an emergency measure, may breathe air through the hose 81 from the interior of his own buoyancy chamber. In such circumstances, of course, the diver will also be taking whatever steps are necessary to return as promptly as can be safely achieved to the surface.

Upon ascending towards the surface, as the external pressure falls, so the volume of gas within the breathing circuit will increase and, in order to avoid rupture of the counterlungs 16, 24 or of any of the hoses, an excess-pressure valve 83 is provided on the exhalation counterlung 16. This valve acts automatically to open to allow pressure in excess of that determined by its calibration to escape from the system. This valve is calibrated to open at a predetermined excess pressure by choice of a suitable biasing spring closing the valve, and has a body with a long pitch helical thread allowing the spring to be "backed off" to a predetermined second position at which the valve opens when there is a much lower pressure differential across it. In either position the valve may be opened manually, for example by a pull cord 84. By providing the two settings it is possible for the diver readily to convert the valve from its normal, low pressure-relief setting to a high pressure-relief setting allowing the equipment to be leak tested on the surface. Thus, the low setting is used during the dive to maintain the counterlungs and the user's lungs at a pressure less than 60 mbar (which is the maximum lung over-pressure admissible) whilst the high pressure setting (138 mbar) is used for leak testing prior to the dive and to achieve full buoyancy at the surface which makes it possible for the counterlungs to be used as a buoyancy aid when the diver is not breathing from the apparatus. The change from the high pressure to the low pressure setting is achieved by a rotation of an outer rotary member through 260°. The pull cord 84 operates an override valve which is incorporated to allow the user to dump gas from the counterlungs at any time during diving should that be necessary, particularly during the ascent.

What is claimed is:

1. Self-contained breathing apparatus of the type having a container (16) for receiving exhaled gas having an oxygen content, means (19) for removing carbon dioxide from the exhaled gas, oxygen sensor means (51, 52, 53) for detecting the oxygen content of the exhaled gas, the sensor means providing output signals indicative of the oxygen content, and means (20, 22) for injecting oxygen into the exhaled gas to reinstate the oxygen content so as to lie within a desired range for re-breathing, characterised in that the signals from the oxygen sensor means (51, 52, 53) are delivered to two independent signal processing circuits (59, 60) which are interconnected in a primary and secondary relationship with the primary signal processing circuit acting in use to control a solenoid valve (22) for injection of oxygen into the exhaled gas and the secondary signal processing circuit acting in use to display (61, 62) information concerning the sensor output signals to provide confirmation of the satisfactory operation of the primary signal processing circuit wherein either of said signal processing circuits may function as the primary signal processing circuit while the other of the signal processing circuits may function as the secondary signal processing circuit.

2. Self-contained breathing apparatus as claimed in claim 1, in which the signal processing circuits are interconnected with a signal line and the secondary signal processing circuit constantly monitors the operation of the primary signal processing circuit.

3. Self-contained breathing apparatus as claimed in claim 2, in which each signal processing circuit has an independent on/off switch and is programmed to adopt the role of primary circuit if the other one of the signal processing circuits is not switched on subject to a power failure.

4. Self-contained breathing apparatus as claimed in claim 1, characterised in that the oxygen sensor means comprise three independent sensors housed in a chamber through which the exhaled gas flows in use of the apparatus, and the output signals of the sensors are delivered to signal processing circuits which act to determine a partial pressure value of oxygen in the gas in the chamber by taking an average value of two sensor signals which are nearest to one another in value.

5. Self-contained breathing apparatus as claimed in claim 1, in which the primary signal processing circuit acts to maintain an oxygen partial pressure of not less than 0.5 bar.

6. Self-contained breathing apparatus as claimed in claim 1, in which the signals are processed at a sampling frequency which is maintained at a level such that the solenoid valve controlled by the output signal from the sensors may be activated immediately in response to a change in the oxygen content.

7. Self-contained breathing apparatus as claimed in claim 1, in which three oxygen sensors are positioned spaced around a central location in a chamber, facing inwardly of a chamber periphery and each provided with an individual moisture deflector.

8. Self-contained breathing apparatus as claimed in claim 7, in which the oxygen sensors comprise vibration-proof electrical connector devices.

9. Self-contained breathing apparatus as claimed in claim 1, further including a source of a breathable diluent gas.

10. Self-contained breathing apparatus as claimed in claim 1, in which the container for receiving exhaled gas is part of a counterlung separated into two independent chambers including a first chamber for receiving exhaled gas from a mouthpiece and a second chamber for receiving gas from the carbon dioxide removing means, after introduction of oxygen, to act as a temporary store of gas reconditioned for breathing, characterised in that the first and second chambers are connected to the mouthpiece by hose couplings incorporating two unidirectional valves orientated to ensure that air exhaled into the mouthpiece is directed only to the first chamber and air inhaled through the mouthpiece arrives only from the second chamber, and in which the hose couplings comprise respective T-couplings which are swivelable to allow free movement of the air hoses.

11. Self-contained breathing apparatus as claimed in claim 10, in which the T-coupling between each air hose and the counterlung includes an internal baffle directing air within the hose to or from the counterlung and further acting as a moisture trap.

12. Self-contained breathing apparatus as claimed in claim 10, in which the swivelable T-couplings are releasable from the air hoses.

13. Self-contained breathing apparatus as claimed in claim 1, in which the means for removing carbon dioxide from the exhaled gas comprises a filter bed housed between water resistant gas-permeable barriers in a container.

14. Self-contained breathing apparatus as claimed in claim 1, in which the container for receiving exhaled gas is flexible and inflatable.

15. Self-contained breathing apparatus as claimed in claim 14, in which the flexible container for receiving exhaled gas is a shaped counterlung adapted to pass over a shoulder of a diver utilising the apparatus.

16. Self-contained breathing apparatus as claimed in claim 1, in which the signal processing circuits include monitors for detecting if the oxygen content departs from a predetermined range whereby to provide an alarm signal, and an audible alarm indicator is positioned so as to be close to an ear of the diver using the apparatus when the apparatus is worn.

17. Self-contained breathing apparatus as claimed in claim 16, in which there is further provided a visible alarm indicator linked to the audible indicator whereby to provide an additional warning indication.

18. Self-contained breathing apparatus as claimed in claim 1, further comprising air hoses leading to or from a mouthpiece wherein the air hoses comprise flexible elongate tubular members maintained in an arcuate curved shape by a pre-shaped sleeve.

19. Self-contained breathing apparatus as claimed in claim 1, in which the means for removing carbon dioxide, the oxygen sensors and control valve, a container housing a source of oxygen under pressure, and a container housing a breathable diluent gas are all supported on a panel having straps by means of which the apparatus can be carried on a diver's back in use.

20. Self-contained breathing apparatus as claimed in claim 19, in which the containers for oxygen and diluent gas, as well as the carbon dioxide removal apparatus, are all housed in a substantially rigid casing.

* * * * *